United States Patent
Wienand et al.

(10) Patent No.: US 10,107,221 B2
(45) Date of Patent: Oct. 23, 2018

(54) METHOD FOR PRODUCING A SOOT SENSOR WITH A LASER BEAM

(71) Applicant: Heraeus Sensor Technology GmbH, Hanau (DE)

(72) Inventors: Karlheinz Wienand, Aschaffenburg (DE); Matsvei Zinkevich, Goldbach (DE); Dieter Teusch, Bruchköbel (DE)

(73) Assignee: Heraeus Sensor Technology GmbH, Hanau (DE)

( * ) Notice: Subject to any disclaimer, the term of this patent is extended or adjusted under 35 U.S.C. 154(b) by 11 days.

(21) Appl. No.: 14/772,480

(22) PCT Filed: Feb. 28, 2014

(86) PCT No.: PCT/EP2014/053933
§ 371 (c)(1),
(2) Date: Sep. 3, 2015

(87) PCT Pub. No.: WO2014/135450
PCT Pub. Date: Sep. 12, 2014

(65) Prior Publication Data
US 2016/0017830 A1      Jan. 21, 2016

(30) Foreign Application Priority Data

Mar. 6, 2013  (DE) .................. 10 2013 102 200
Mar. 6, 2013  (DE) .................. 10 2013 102 201
Sep. 18, 2013 (DE) .................. 10 2013 110 291

(51) Int. Cl.
*G01N 15/06*     (2006.01)
*F02D 41/14*     (2006.01)
(Continued)

(52) U.S. Cl.
CPC ......... *F02D 41/1466* (2013.01); *G01K 13/02* (2013.01); *G01N 15/06* (2013.01);
(Continued)

(58) Field of Classification Search
CPC ........ G01N 15/0656; G01N 2015/0046; F01N 2560/05; F02D 41/1466
See application file for complete search history.

(56) References Cited

U.S. PATENT DOCUMENTS 4,656,832 A * 4/1987 Yukihisa ................ F01N 3/027
                                                        324/717
7,954,230 B2 * 6/2011 Nelson .................. H01C 17/24
                                                        29/610.1
(Continued)

FOREIGN PATENT DOCUMENTS

DE        10331838 B3    9/2004
DE    102006047927 A1    4/2008
(Continued)

OTHER PUBLICATIONS

International Preliminary Report on Patentability dated Sep. 17, 2015 in International Application No. PCT/EP2014/053933.
(Continued)

*Primary Examiner* — Blake A Tankersley
(74) *Attorney, Agent, or Firm* — Panitch Schwarze Belisario & Nadel LLP

(57) ABSTRACT

A method for producing a soot sensor is provided. The method includes steps of applying a contiguous metallic layer on an electrically insulating substrate and structuring the metal coating with a laser beam by vaporizing areas of the metallic layer. At least two interlaced contiguous electrically conductive structures are produced. The electrically conductive structures are spatially separated from one another with the laser beam and are electrically insulated from one another such that the conductive structures substantially extend next to one another and close to one another in an area relative to a total length thereof. A soot sensor produced using such a method is also provided. The soot sensor has an electrically insulating substrate and at least
(Continued)

two contiguous electrically conductive structures which are spatially separated from one another and are interlaced as structured metallic layers. An intermediate space between the conductive structures is burned free with a laser.

15 Claims, 7 Drawing Sheets

(51) Int. Cl.
  *G01K 13/02* (2006.01)
  *G01N 25/72* (2006.01)
(52) U.S. Cl.
  CPC ......... *G01N 15/0656* (2013.01); *G01N 25/72* (2013.01); *G01K 2013/024* (2013.01)

(56) References Cited

U.S. PATENT DOCUMENTS

| | | | |
|---|---|---|---|
| 7,998,666 B2 | 8/2011 | Stiene et al. | |
| 8,357,274 B2 | 1/2013 | Marquant et al. | |
| 2002/0014107 A1 | 2/2002 | Moos et al. | |
| 2008/0190173 A1 | 8/2008 | Wienand et al. | |
| 2009/0217737 A1 | 9/2009 | Dorfmueller et al. | |
| 2010/0170843 A1* | 7/2010 | Yamato | B01D 63/023 210/323.1 |
| 2011/0156727 A1* | 6/2011 | Achhammer | F02D 41/1466 324/691 |
| 2012/0324981 A1* | 12/2012 | Hedayat | G01N 15/0656 73/23.33 |

FOREIGN PATENT DOCUMENTS

| | | |
|---|---|---|
| DE | 102007033213 A1 | 1/2009 |
| DE | 102007038680 A1 | 2/2009 |
| DE | 102007047078 A1 | 4/2009 |
| EP | 2065903 A1 | 6/2009 |
| EP | 2208982 A2 | 7/2010 |
| JP | S6218655 U | 2/1987 |
| JP | H04216452 A | 8/1992 |
| JP | H08260077 A | 10/1996 |
| JP | H09318577 A | 12/1997 |
| JP | 2009085959 A | 4/2009 |
| JP | 2009524805 A | 7/2009 |
| JP | 2011501127 A | 1/2011 |
| JP | 2012037285 A | 2/2012 |
| JP | 2012047722 A | 3/2012 |
| WO | 0125775 A1 | 4/2001 |
| WO | 2009010389 A1 | 1/2009 |
| WO | 2009021734 A1 | 2/2009 |
| WO | 2009049091 A2 | 4/2009 |
| WO | 2011106625 A1 | 9/2011 |

OTHER PUBLICATIONS

International Search Report and Written Opinion dated May 28, 2014 in International Application No. PCT/EP2014/053933.
English translation of Office Action dated Jun. 28, 2016 in KR Application No. 10-2015-7027482.
Office Action dated May 11, 2017 in CN Application No. 201480012656.3.
English Summary of Relevant Portion of Office Action dated May 11, 2017 in CN Application No. 201480012656.3.

* cited by examiner

METHOD FOR PRODUCING A SOOT SENSOR WITH A LASER BEAM

CROSS-REFERENCE TO RELATED APPLICATIONS

This application is a Section 371 of International Application No. PCT/EP2014/053933, filed Feb. 28, 2014, which was published in the German language on Sep. 12, 2014, under International Publication No. WO 2014/135450 A1 and the disclosure of which is incorporated herein by reference

BACKGROUND OF THE INVENTION

The present invention relates to a method for producing a soot sensor and to a soot sensor produced according to such a method.

Soot sensors are used to control or regulate the combustion process of engines, in particular of diesel engines and oil heaters. Depending on the quantity of soot particles, the combustion may be controlled such that fewer soot particles occur and/or combustion is more efficient.

DE 10 2007 038 680 A1 discloses a soot sensor in which a conductive track structure is applied on a smooth $Al_2O_3$ surface. Such a structure simplifies the adsorption of soot particles.

From WO 2011/106625 A1, a soot sensor is known which is designed with a heating element and a sensor element on a substrate. The electrical resistance between the heating element and the sensor element changes if soot particles settle on the surface of the soot sensor. It is therefore possible to determine the concentration of soot particles on the surface and, therefore, in the flow of exhaust gas. The heating element is heated to a sufficiently high temperature in order to burn free the sensor.

Additional sensors may also be used to control the combustion process, such as lambda probes or temperature sensors, for example. Continuously increasing requirements regarding the reduction of soot emissions are demanded on soot sensors for controlling diesel engines. For example, the so-called EU6 Guideline requires that vehicles operated by diesel engines have very low quantities of soot. Such low soot quantities are very difficult to detect using the known soot sensors due to the low number of soot particles; i.e., due to the very low concentration of soot particles in the flow of exhaust gas.

The disadvantage of the known soot sensors, therefore, is that such soot sensors do not react with sufficient sensitivity to be capable of meeting the increasingly stricter requirements. Another disadvantage of the known sensors is that a large number of sensors must be installed in the flow of exhaust gas, such that a large number of connecting terminals is required. At the same time, however, there is always a desire to produce the engines or the combustion systems in a manner that is as simple and as cost effective as possible. The sensors themselves should also be as cost effective as possible. Furthermore, the sensors should be robust and error-free when installed in the exhaust gas system.

BRIEF SUMMARY OF THE INVENTION

One problem addressed by the present invention is therefore to overcome the disadvantages of the prior art. In particular, an objective of the present invention is to provide a sensor which reacts with sufficient sensitivity to detect small quantities of soot, but which is also simultaneously a simplification of existing sensors. The sensor is preferably compact and robust for installation and may be produced at a low cost. Further advantages of the present invention, which are not mentioned above, become readily apparent from the overall context of the present invention.

Some of the problems addressed by the present invention are solved by a method for producing a soot sensor. The method comprises the steps of:

applying a contiguous metallic layer on an electrically insulating substrate; and structuring the metal coating with a laser beam by vaporizing areas of the metallic layer, wherein at least two interlaced contiguous electrically conductive structures are produced and the electrically conductive structures are spatially separated from one another with the laser beam and are electrically insulated from one another in such a manner that the conductive structures substantially extend next to one another and close to one another in this area relative to the total length thereof.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

DETAILED DESCRIPTION OF THE INVENTION

Figure 1:
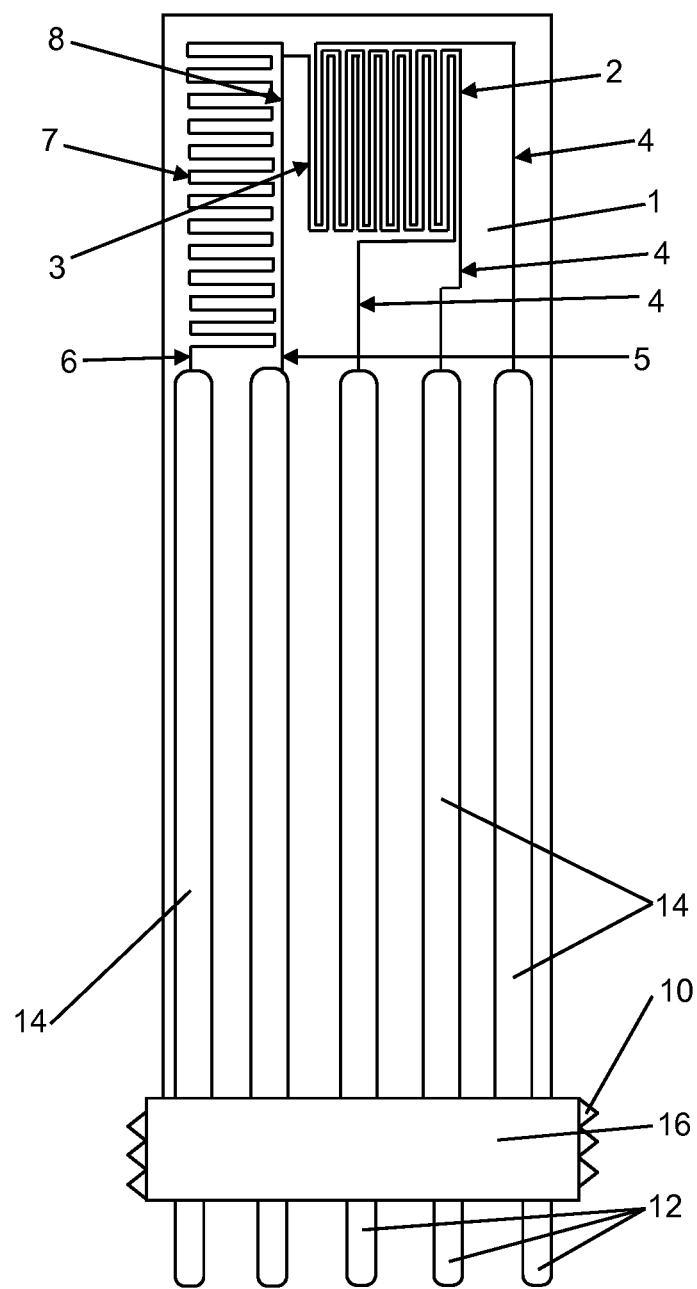
FIG. 1 shows a schematic top view of a soot sensor including a temperature sensor, according to an embodiment of the present invention.

For simplicity, the same reference numbers are used for the same components in all the figures, even though the components may differ slightly and the components labeled with the same reference numerals are not always entirely similar.

Within the scope of the present invention, the phrase "at least two interlaced contiguous electrically conductive structures" is intended to mean two or more layers, which are separate but each of which is contiguous, conductive and, in particular, metallic, and which are shaped such that they extend close to one another over a large area of the structures.

Within the scope of this application, the term "interlaced" is intended to mean that at least two structures are arranged such that one structure is arranged so as to be parallel, perpendicular, and/or at an angle with respect to the other structure. As an alternative or in addition, it is possible that one structure is arranged in any type of free form; e.g., in a curved shape, an elliptical shape, or the like, relative to the other structure. In this way, it is possible that at least a subregion or the entire region of the respective structure is thusly arranged. It is also possible to arrange the structures in a planar manner; i.e., in a plane, or spatially (i.e., in three dimensions), relative to one another in accordance with the preceding statements. For example, it is possible to arrange two structures in a plane so as to be interlaced with respect to one another such that the structures are arranged to as to be intermeshed with one another, as in a gearwheel, wherein the structures are spaced apart from one another, in particular with a spacing distance of less than 50 μm, preferably less than 30 μm.

According to an embodiment of the present invention, it is preferably provided that the contiguous metallic layer is applied on the electrically insulating substrate using a thick-layer process. Preferably, a noble metal thick layer is applied, and particularly preferably a platinum thick layer is applied.

According to an embodiment of the present invention, the spacing distance between the conductive structures is preferably less than 50 μm, particularly preferably between 10 μm and 30 μm. As used herein, the phrase "close to one another" is therefore intended to mean less than 80 μm, preferably less than 50 μm.

In methods according to embodiments of the present invention, the metallic layer may be applied onto the electrically insulating substrate in a prestructured manner. Preferably, at least the widened conductive layers are prestructured for the electrical contacting of the conductive structures. In this connection, it may be particularly preferable that all of the leads are prestructured to form conductive structures.

The production of the soot sensor is simplified when only the narrow separating regions between the conductive structures are vaporized by the laser beam and the coarser structures are created directly during application (e.g., by printing).

According to an embodiment of the present invention, the laser beam is moved in a line, preferably in a meandering line, along the spacing between the conductive structures to be created above the metallic layer, and thereby vaporizes the metallic layer along this line. In this connection, the spacing between the finally structured, conductive structures may preferably correspond to the diameter of the effective cross section of the focal spot of the laser beam.

By this method, the spacing between the conductive structures is kept as small as possible. At the same time, the laser beam or the focal spot of the laser beam may be moved very rapidly and relatively effortlessly over the metallic layer in order to create the separation of the metallic layer into two conductive structures. This simplifies and lowers the cost of production.

According to an embodiment of the present invention, the conductive structures preferably extend next to one another along at least 90% of their entire length, preferably along at least 98% of their entire length.

The expression "the conductive structures extend substantially next to one another along their entire length and, in this region, extend closely to one another" is intended to mean that the conductive structures extend next to one another along at least 90% of their entire length and, in this region, extend closely to one another, i.e., preferably less than 50 μm apart from one another.

The greater the parallel portions of the conductive structures are, the more sensitive the soot sensor is to a resistance measurement or to a capacitive measurement or a measurement of the electrical insulation losses between the two conductive structures for determining the concentration of soot particles in the gas flow.

In the method according to an embodiment of the present invention, a metal oxide substrate or a glass substrate or a glass ceramic substrate, preferably a ceramic $Al_2O_3$ substrate or a glass, glass ceramic, or $Al_2O_3$ layer, is used as the electrically insulating substrate.

These materials are particularly well suited for constructing a soot sensor, which is intended for use in the hot and chemically aggressive environment of an exhaust gas flow. In addition, metallic layers applied on these layers may be burned away particularly well using the laser beam without the laser beam causing further damage.

In addition, a temperature sensor may be disposed on the side of the electrically insulating substrate opposite the metal coating or soot sensor or adjacent to the conductive structures on the electrically insulating substrate.

Due to the combination of the soot sensor with another sensor, only one connecting terminal is needed for both sensors when installed in an exhaust gas system. In addition, the temperature sensor measures the temperature at the site where the conductive structures are also located. It is thereby possible to more exactly determine the status of the soot sensor during the measurement and during "burning free" the soot sensor. Furthermore, the temperature of the exhaust gas and the concentration of soot particles may be determined individually but also simultaneously.

Preferably, after the structuring of the conductive structures, the leads of the conductive structures are coated entirely and, more preferably, the conductive structures are coated in certain areas with an insulating layer of a metal oxide, glass, or a glass ceramic and, preferably, the temperature sensor is fastened on the insulating layer, particularly preferably by use of glass solder.

By applying the insulating layer as a protective layer, the metallic areas of the soot sensor are protected (i.e., are not forced to be exposed to the chemically aggressive environment of the exhaust gas flow). This layer may also be used, ideally, to fasten the additional temperature sensor in order to form a combination sensor.

Furthermore, a temperature sensor may be first formed on a ceramic substrate, preferably using thin-layer technology, and the electrically insulating substrate is then applied as a layer onto the temperature sensor, and the contiguous metallic layer is then applied onto the electrically insulating substrate to create the conductive structures, wherein a layer of $Al_2O_3$ or glass or glass ceramic is preferably applied on the temperature sensor as the electrically insulating substrate.

By such a production method, a soot sensor having a temperature sensor is created, in which components of the temperature sensor, preferably components made of at least one metal or a metal alloy, are protected against the surroundings, in the manner of a sandwich, by the ceramic substrate and by the electrically insulating substrate on which the conductive structures are disposed. It is thereby possible to apply the metals used to produce the temperature sensor using thin-layer technology without this impairing the stability of the sensor.

According to an embodiment of the present invention, the layer structure is fastened on a connecting terminal, wherein the conductive structures and, preferably, the temperature sensor as well are electrically contacted to contact elements of the connecting terminal.

Due to the connecting terminal and the contacting, the soot sensor is particularly easy to install.

According to a preferred embodiment of the present invention, interlaced heating spirals or electrodes may be formed as conductive structures.

The problems addressed by the present invention are also solved by a soot sensor produced using such a method, in which the soot sensor has an electrically insulating substrate and at least two contiguous electrically conductive structures, which are spatially separated from one another and are interlaced, as structured metallic layers, wherein the intermediate space between the conductive structures is burned free with a laser, the intermediate space is preferably smaller than 50 μm at least in certain areas, and the conductive structures are contacted to widened conductive layers.

In one embodiment, at least the widened conductive layers are covered with an insulating layer, and preferably the areas of the conductive structures adjacent to the widened conductive layers are covered with an insulating layer.

By applying the insulating layer as a protective layer, metallic areas of the soot sensor are protected, which do not necessarily have to be exposed to the chemically aggressive environment of the exhaust gas flow. This layer may also be used, ideally, to fasten the additional temperature sensor in order to create a combination sensor.

According to an embodiment of the present invention, the soot sensor has a connecting terminal and a temperature sensor, wherein the conductive structures are disposed, as a structured metallic layer, on the electrically insulating substrate and are covered, at least in certain areas, with an insulating layer, wherein the temperature sensor is disposed, as a structured metallic layer, on the insulating layer or the conductive structures and the temperature sensor are disposed on the same electrically insulating substrate, wherein the temperature sensor and the conductive structures are electrically and mechanically connected to the connecting terminal.

The thusly designed soot sensor or combination sensor has the advantages mentioned above with respect to the method according to an embodiment of the present invention.

According to an embodiment of the present invention, the electrically insulating substrate is a ceramic metal oxide substrate, in particular comprising $Al_2O_3$, magnesium oxide, zirconium oxide, yttrium oxide, and/or $SiO_2$, preferably a ceramic $Al_2O_3$ substrate.

These materials are thermally and mechanically stable and, due to their insulating effect, are well suited for constructing soot sensors according to the invention.

In addition, the conductive structures are preferably precious metal thick layers structured using a laser, preferably platinum thick layers, and/or the conductive structures have an electrical resistance of at least 1 Ohm and at most 10 Ohm, at 0° C.

Such a thick layer and these electric resistances are suitable for heating the soot sensor or for burning off soot particles, as well as for measuring the electrical resistance between the conductive structures.

Particularly preferably, the conductive structures are interlaced heating spirals or electrodes.

According to an embodiment of the present invention, the soot sensor may be preferably designed so as to have two interlaced contiguous conductive structures. Since the intermediate spaces between the conductive structures are cut using a laser, the spacings between the conductive structures may be designed to be particularly small, which increases the sensitivity of the soot sensor.

According to an embodiment of the present invention, the sensor comprises at least one second temperature sensor and/or at least one second soot sensor, which are or is preferably connected to connecting terminal, particularly preferably to the contact elements.

In a soot sensor comprising a temperature sensor, according to an embodiment of the present invention, the connecting terminal has a fastening mechanism, in particular a screw thread and/or a flange, wherein the ceramic substrate is connected to the fastening mechanism in a mechanically fixed manner, preferably via a glass, and the connecting terminal has an electrical contacting mechanism, in particular a plug having at least three contact pins and/or sockets, preferably having five or six contact pins and/or sockets, wherein the temperature sensor and the soot sensor are electrically contacted to the contacting mechanism.

Due to the fixed connection to the connecting terminal, it is ensured that the soot sensor may be easily inserted when installed on an exhaust gas system.

According to an embodiment of the present invention, the electrically insulating substrate may also be fixedly connected to the connecting terminal via a second substrate. Thus, the electrically insulating substrate itself is fixed to the connecting terminal or the second substrate is fixed to the connecting terminal, wherein the second substrate is fastened to the electrically insulating substrate. In the second case, the electrically insulating substrate is thereby also rigidly and fixedly connected to the connecting terminal, namely via the second substrate.

According to an embodiment of the present invention, the temperature sensor is a thin layer or a thick layer, which contains platinum or consists of platinum. According to the invention, it can also be provided that the temperature sensor has an electrical resistance of at least 50 Ohm and at most 2000 Ohm, at 0° C.

These layers or these resistances make it possible to design a particularly suitable temperature sensor as a resistance temperature sensor in the form of a resistor meander. The temperature sensors are relatively accurate due to this design.

In addition, the insulating layer covering the temperature sensor or the soot sensor at least in certain areas consists of a metal oxide or a glass or a glass ceramic.

Such insulating layers are mechanically and chemically particularly stable and are therefore well suited for constructing a soot sensor according to an embodiment of the present invention. The chemical stability of the soot sensor is advantageous for the stability of the soot sensor due to the chemically aggressive environment in the gas flow of a combustion engine, in particular a diesel engine.

In addition, a soot sensor having a temperature sensor is provided, in which the temperature sensor has greater electrical resistance than the conductive structures. Preferably, the temperature sensor has electrical resistance that is higher than that of the conductive structures by a factor of five, more preferably having electrical resistance that is higher than that of the conductive structures by a factor of forty to eighty.

Given these resistance ratios, the temperature sensor may measure with high accuracy and the soot sensor having the conductive structures may be burnt off well.

According to an embodiment of the present invention, the temperature sensor is a thermocouple, wherein the thermocouple is designed as a structured metallic layer made from at least two different interconnected metals and/or alloys, which are disposed on the ceramic substrate.

Thermocouples make it possible to determine the temperature with high accuracy, independently of the conductive structures of the soot sensor. Surprisingly, it was found that the thermoelectric wires may be applied on the ceramic substrate or the insulating layer as a thin layer or a thick layer and may be used to measure the temperature.

According to a particularly preferred embodiment of the present invention, the soot sensor is disposed, as a structured metallic layer, on the insulating layer, which covers the temperature sensor arranged on a ceramic substrate at least in certain areas and preferably completely, wherein the conductive structures of the soot sensor do not cover the temperature sensor, but rather are disposed only on the areas of the insulating layer that do not directly cover the temperature sensor. Preferably, the temperature sensor frames the conductive structures in a plane offset by the insulating layer.

Furthermore, in the soot sensors according to an embodiment of the present invention, the conductive structures are disposed on a ceramic substrate and the temperature sensor is applied on a second metallic substrate having an insulating coating, wherein the temperature sensor is disposed on the insulating coating (of the second, metallic substrate), or the second substrate is a ceramic or oxidic, insulating substrate, on which the temperature sensor is directly disposed.

A design having such a multilayer may be designed more compact. At the same time, a temperature sensor located on the inside is better protected against the chemically aggressive environment of the exhaust gas flow.

A problem addressed by the present invention is also solved by an engine, in particular a diesel engine, having such a soot sensor, wherein the soot sensor is fastened to the connecting terminal at an opening in an exhaust gas line such that the soot sensor is disposed in the exhaust gas flow of the engine.

Methods according to embodiments of the present invention for producing a soot sensor including a temperature sensor may be obtained for example by having the following method steps of:

applying a structured metallic layer, as the temperature sensor, on a ceramic substrate;

covering the temperature sensor with an insulating layer, preferably a glass or glass ceramic layer;

applying a metallic coating, preferably a precious metal thick layer onto areas of the insulating layer; and structuring the metallic coating using a laser beam to form at least two interlaced contiguous conductive structures in order to form a soot sensor.

As an alternative, the following method steps may also be implemented:

applying a structured metallic layer, as the temperature sensor, on a first side of a ceramic substrate;

applying a metallic coating on the second side of the ceramic substrate; and structuring the metallic coating using a laser beam to form at least two interlaced contiguous conductive structures in order to form a soot sensor.

In another alternative, the following method steps may also be implemented:

applying a metallic coating on a ceramic substrate;

structuring the metallic coating using a laser beam to form at least two interlaced contiguous conductive structures in order to form a soot sensor; and applying a structured second metallic layer, as the temperature sensor, on the ceramic substrate adjacent to the conductive structures or around the conductive structures.

In yet another alternative, the following method steps may also be implemented:

applying a metallic coating on a ceramic substrate;

structuring the metallic coating using a laser beam to form at least two interlaced contiguous conductive structures in order to form a soot sensor;

applying a structured second metallic layer, as the temperature sensor, on a second substrate; and fastening, preferably gluing, the second substrate onto the ceramic substrate.

In addition, the fastening of the layer structure on a connecting terminal may be provided as another method step in all the methods according to the present invention, wherein the temperature sensor and the soot sensor are electrically contacted to contact elements of the connecting terminal.

The present invention is based on the surprising findings that producing a soot sensor from a contiguous metallic layer using a laser beam makes it possible to provide a particularly sensitive soot sensor for determining the density of soot particles in an exhaust gas flow, which may be used to control or regulate a combustion process, in particular the combustion in a diesel engine. Due to the small spacing distances between the conductive structures, which may be created quickly and at low cost using the laser beam, the soot particles adsorbed on the surface of the soot sensor in the region of the conductive structures result in a greater change in resistance or change in permittivity and, therefore, the sensor reacts with greater sensitivity. Due to the combination with a temperature sensor in a layered component, the installation of an additional separate sensor may be omitted. In addition, the same substrate and even a portion of the conductor structure may be used jointly to produce the soot sensor. As a result, the soot sensor with the temperature sensor may be produced at lower cost than is possible for the two sensors individually.

If the soot sensor is produced on a protective layer on the temperature sensor, the temperature sensor may also be constructed with a more sensitive thin layer, since the temperature sensor is protected against the chemically aggressive environment in the exhaust gas flow, without reservations or any additional protective measures. Since the structure of the conductive structures is formed using a laser, it is particularly advantageous when the soot sensor and the temperature sensor are not disposed directly above one another, thereby ensuring that the laser beam does not cut through the protective layer when forming the structure of the conductive structures, which would damage the thin layer or the thick layer of the temperature sensor.

When the conductive structures and the temperature sensor share a portion of a conductive structure, one of the contact elements or a pin or a socket for the connecting terminal may be omitted. In addition, some material for the lead structure may be saved. When performing the measurement with the two sensors or when burning off the soot sensor, it is only necessary to use the correct contact elements and, therefore, the correct connecting terminals of the two sensors such that an electrical voltage is applied or measured at the desired connecting terminals.

Basically, it is also possible to use a common part of a conductor structure on the ceramic substrate when the temperature sensor and the conductive structures are not disposed on the same side of the ceramic substrate. Preferably, this may be achieved according to the present invention in that a through-plating is used, which connects the conductor structure on a first side of the substrate to the common part of the conductor structure on the second side of the substrate.

Extremely adhesive and corrosion-resistant platinum thick layers cannot be screen-printed with the preferred small spacing distances.

The laser makes it possible to create particularly small spacing distances between the conductive structures of the soot sensor. Due to the small spacing distances, the soot sensor is particularly sensitive such that, even when only a few soot particles settle, there is already a measurable change in the electrical DC resistance or the permittivity in the soot sensor. The soot sensor created using the laser and, therefore, having small spacing distances between the conductive structures therefore has greater sensitivity than conventional soot sensors.

It is possible, as an alternative, to use the sensor according to the present invention in the field of investigating at least one liquid. To this end, the sensor is preferably designed as a dielectric sensor, which is also known as an impedance sensor, wherein, for example, the quality of the liquid and/or the foreign particle content of the liquid is measured by the sensor. Liquids may be, for example, oils, greases, or fluids in general. Preferably, oils or greases, such as greases for frying in gastronomy or oils in the automotive field (e.g., motor oils for passenger cars or trucks) are investigated. Accordingly, embodiments of the present invention relate to a sensor to be used in the field of investigating at least one liquid and the production of such a sensor.

FIG. 1 shows a schematic top view of a soot sensor according to an embodiment of the present invention. Metallic structures made from platinum or a platinum alloy are applied on an electrically insulating substrate 1 made from aluminum oxide or another metal oxide. Two interlaced heating spirals 2, 3, as metallic structures, are disposed on the insulating substrate 1. The heating spirals 2, 3 are electrically contacted to leads 4, 5. The heating spirals 2, 3 and the leads 4, 5 already form a soot sensor on the electrically insulating substrate 1.

The lead 5 and the lead 6 form the electrical contact for a meandering structure, which forms a temperature sensor 7 on the ceramic substrate 1. The lead 5 is therefore a common lead 5 for one of the heating spirals 3 as well as for the temperature sensor 7. The temperature sensor 7 is a platinum resistor structure having a high (i.e., higher by ten-fold to one hundred-fold) electrical resistance as compared to the heating spirals 2, 3.

The combination sensor formed by the heating spirals 2, 3 and the temperature sensor 7 may be fastened via a thread 10 in an opening of an exhaust gas pipe (not shown) having a suitable mating thread or via a holder having a corresponding mating thread. The temperature sensor 7 and the heating spirals 2, 3, in the installed state thereof, point into the interior of the exhaust gas pipe. On the exterior, the soot sensor has five plugs 12, which are electrically connected to the leads 4, 5, 6.

All the leads 4, 5, 6 extend into widened conductive layers 14, which are disposed between the leads 4, 5, 6 and the plugs 12. By such widening, it is ensured that the electrical resistance is caused primarily by the temperature sensor 7 and the heating spirals 2, 3 and, therefore, the electrical voltage drops substantially at the temperature sensor 7 and the heating spirals 2, 3. The length of the insulating substrate 1 and the widened conductive layers 14 (from the top to the bottom in FIG. 1) serves the purpose of thermally insulating the soot sensor toward the connecting terminal 16, which includes the plugs 12 and the thread 10.

The conductive tracks of the heating spirals 2, 3 and the leads 4, 5, 6 of the temperature sensor 7, and a common part 8, which is used both as a lead to the heating spiral 3 and to the temperature sensor 7, are shown only as lines in FIG. 1. The width of the lines does not correspond to the actual width of the conductive tracks. The spacing distances between the heating spirals 2, 3 are substantially finer according to an embodiment of the present invention than can be depicted in the overview of the schematic FIG. 1.

The plugs 12 extend through the connecting terminal 16 and are electrically connected to the widened conductive layers 14, for example, in that wires are soldered or welded on. The connecting terminal 16 may be, for example, a ceramic plug having through-holes for wires or having enclosed wires for electrically contacting the plugs 12 to the widened conductive layers 14. The connecting terminal 16 is connected to the insulating substrate 1 in a mechanically fixed and rigid manner by a glazing made from an $SiO_2$-based glass (not shown). The glazing serves the purpose, on the one hand, of connecting the connecting terminal 16 to the insulating substrate 1, but also fixes and protects the connecting wires between the plugs 12 and the widened conductive layers 14 and seals the connecting terminal 16 with respect to the outside (in the direction of the plug 12).

When a measurement is performed, the first step is to measure the electrical DC resistance between the heating spirals 2, 3. When soot particles settle on the surface of the insulating substrate 1 between the heating spirals 2, 3, the electrical resistance between the heating spirals 1, 3 changes. After a previously determined time or after a previously determined change in resistance, the heating spirals 2, 3 are heated with a current to 600° C. to 700° C. As a result, the soot particles on the surface of the insulating substrate 1 burn in the region of the heating spirals 2, 3, i.e., this surface is burned free. The electrical resistance and its change over time may then be determined again in order to determine the soot-particle concentration and its change over time in the exhaust gas flow.

In the pauses therebetween or, if the influences by the operation of the heating spirals 2, 3 are suitably computationally accounted for, simultaneously therewith, the temperature of the exhaust gas flow may be determined by the temperature sensor 7.

The heating spirals 2, 3 and the temperature sensor 7 may also be produced, for example, by first applying a platinum layer or a platinum alloy layer, as a thick layer, on the insulating substrate 1. Next, the structure that is shown is created by a laser or a laser beam, which vaporizes the free areas between the heating spirals 2, 3 shown in FIG. 1 and, if desired, also between the conductors of the temperature sensor 7 and/or the leads 4, 5, 6. The structures that are shown may also be prestructured by a suitable printing method, with which the thick layer is applied, such that only the small spacing distances between the heating spirals 2, 3 of the soot sensor need to be burned free with the laser.

The use of a laser makes it possible to create very narrow spacings between the heating spirals 2, 3 of the soot sensor, which increases the sensitivity of the soot sensor.

Figure 2:
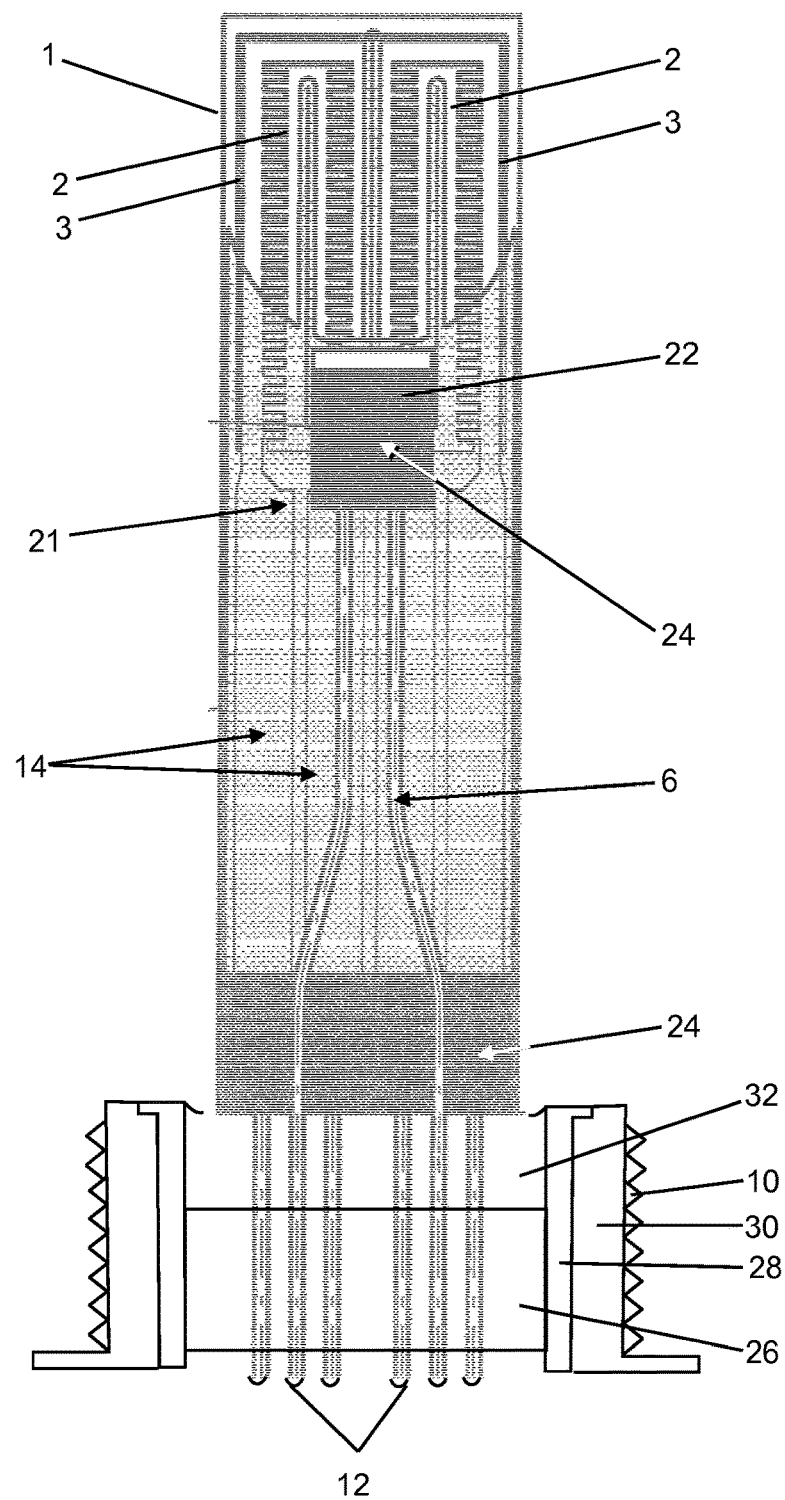
FIG. 2 shows a schematic top view of an alternative soot sensor including a connecting terminal, according to an embodiment of the present invention, in a schematic cross-sectional view.
Figure 3:
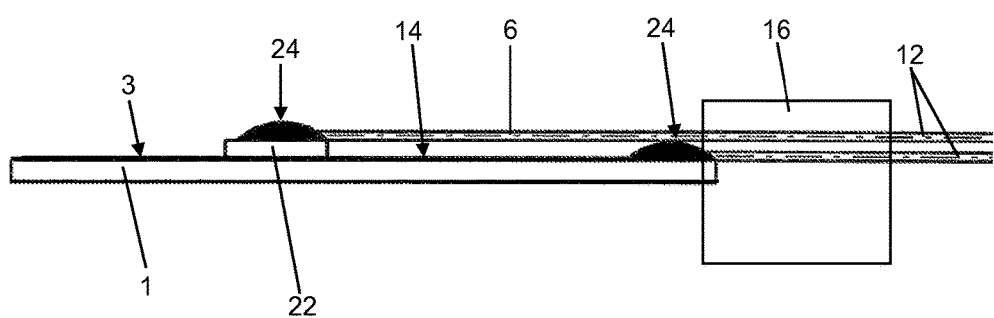
FIG. 3 shows a schematic side view of the soot sensor according to FIG. 2, in accordance with an embodiment of the present invention.

FIG. 2 shows a schematic top view, and more particularly a schematic cross-sectional view of an alternative soot sensor, according to an embodiment of the present invention, comprising a connecting terminal. FIG. 3 shows a schematic side view of the same soot sensor, without the connecting terminal 16 being shown in the same level of detail as in FIG. 2. Therefore, FIG. 2 merely shows a simplified connecting terminal 16, which is illustrated in FIG. 1 in greater detail.

The soot sensor according to FIGS. 2 and 3 has a ceramic substrate 1, on which two soot sensors, each of which has two heating spirals 2, 3, as metal conductive contiguous structures disposed next to one another. The spacing of the heating spirals 2, 3 in relation to one another is created by a laser, which separates the previously contiguous metallic layer into two-times-two separate heating spirals 2, 3.

The heating spirals 2, 3 may be electrically contacted by low resistance, widened conductive layers 14 made from metal. The widened conductive layers 14 and regions of the heating coils 2, 3 are covered with an insulating layer 21. A glass or glass ceramic or aluminum oxide layer, for example, may be applied as the insulating layer 21. By the covering, in certain sections of the heating spirals 2, 3 of the soot sensors, it can be ensured that the exposed regions can reach a temperature that is sufficient for burning free.

A temperature sensor is fastened on the insulating layer 21 by a glass solder. The temperature sensor has a chip, which is disposed on an $Al_2O_3$ substrate 22 and may be electrically contacted to wires 6 as leads. The wires 6 and the connections to the temperature sensor are covered with an insulating strain relief 24 (e.g., a glass ceramic plug). The temperature sensor is a resistor meander on the second substrate 22, although the temperature sensor may also be provided in the form of a thermocouple. Such a strain relief 24 is also provided in the case of the connection of wire terminations 12 to the widened conductive layers 14.

Instead of the $Al_2O_3$ substrate 22, it is also possible to use a glass plate or a metal plate having a glass layer as the second substrate 22. The second substrate 22 and, therefore, the temperature sensor are fastened onto the insulating layer 21 by glass solder independently of the selection of the material of the second substrate 22.

The connecting terminal 16, which is shown in a detailed cross-sectional view in FIG. 2, comprises not only the plugs 12 or the wire terminations 12, but also a cylindrical ceramic block 26 having through-holes for the wire terminations 12. The ceramic block 26 is 10 mm to 20 mm long and the through-holes are thin cylindrical capillary tubes. The wire terminations 12 are tightly connected to the through-holes in that a glazing is provided there, which fills the intermediate spaces in certain areas. The ceramic block 26 is bonded into a cylindrical steel sleeve 28 having a protruding edge. The steel sleeve 28, in turn, is welded to a steel pipe 30. The steel pipe 30 has an external thread 10 and a stop such that the steel pipe 30 may be fixedly screwed, via the thread 10, into an opening in an exhaust gas pipe (not shown) having a corresponding mating thread.

As an alternative, and for all embodiments according to the present invention, a cap nut having an internal thread may also be preferably used as the fastening mechanism, wherein the internal thread may be fastened on an external thread of a pipe connecting piece of the exhaust gas system.

A glazing 32 is provided for sealing the connecting terminal 16 and fixing the ceramic substrate 1, the glazing 32 being fixedly connected to the ceramic block 26, the steel sleeve 28, the wires 12, the lead wires 6 to the temperature sensor and the ceramic substrate 1 or the strain relief 24.

Figure 4:
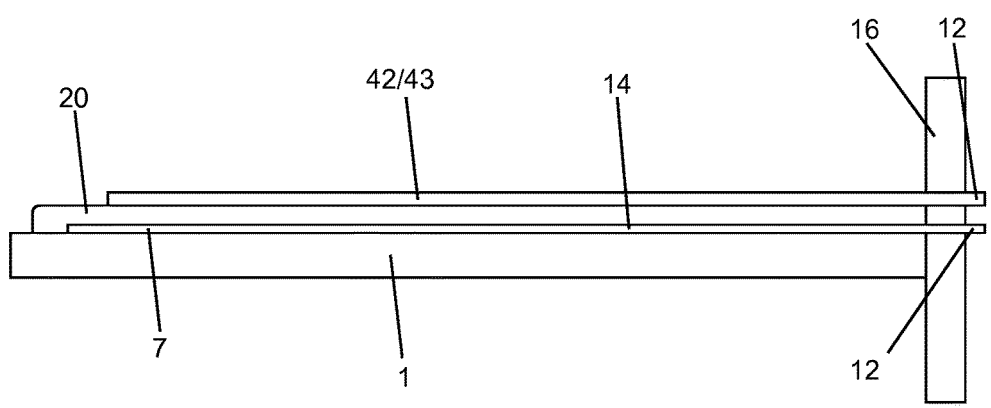
FIG. 4 shows a schematic side cross-sectional view of a third soot sensor, according to an embodiment of the present invention.

FIG. 4 shows a schematic cross-sectional view, from the side, of a third soot sensor according to an embodiment of the present invention. A temperature sensor 7 is applied as a thin layer on a ceramic substrate 1. The temperature sensor 7 may be designed as a resistance temperature sensor in the form of a platinum meander or as a thermocouple having two different metals or alloys.

The temperature sensor 7 is connected to widened, low resistance conductive layers 14, which connect the temperature sensor 7 to a wire, as a plug 12.

An insulating aluminum oxide layer 20 is applied on the temperature sensor 7 and the conductive layers 14. A platinum thick layer is applied (e.g., printed) on this aluminum oxide layer 20, wherein the platinum thick layer is then structured by a laser to form a soot sensor having two interlaced heating spirals 42 or two interlaced comb electrodes 43. In order to avoid damage to the temperature sensor 7 or the leads 14 through the aluminum oxide layer 20 during preparation with the laser, the temperature sensor 7 and, optionally, the leads 14 as well, may be disposed so as to be offset with respect to the soot sensor 2 such that the heating spirals 42 or the electrodes 43 of the soot sensor are not disposed directly above the temperature sensor 7.

The heating spirals 42 or the electrodes 43 may also be electrically connected via wires or plugs 12. The plugs 12 or the wires for contacting the temperature sensor 7 and the heating spirals 42 or the electrodes 43 extend through a common connecting terminal 16, by which the soot sensor may be connected to an exhaust gas system.

In fact, the wires or the plugs 12 and the ceramic substrate 1 are naturally substantially thicker than the thin layer of the temperature sensor 7 or the thick layer of the temperature sensor 7 or the thick layer of the heating spirals 42 or the electrodes 43, although this is not thusly depicted in the schematic illustration according to FIG. 4. The main purpose of the illustration according to FIG. 4 is to show the geometric arrangement of the layer structure and, therefore, this illustration is not shown with the correct thickness ratios.

Figure 5:
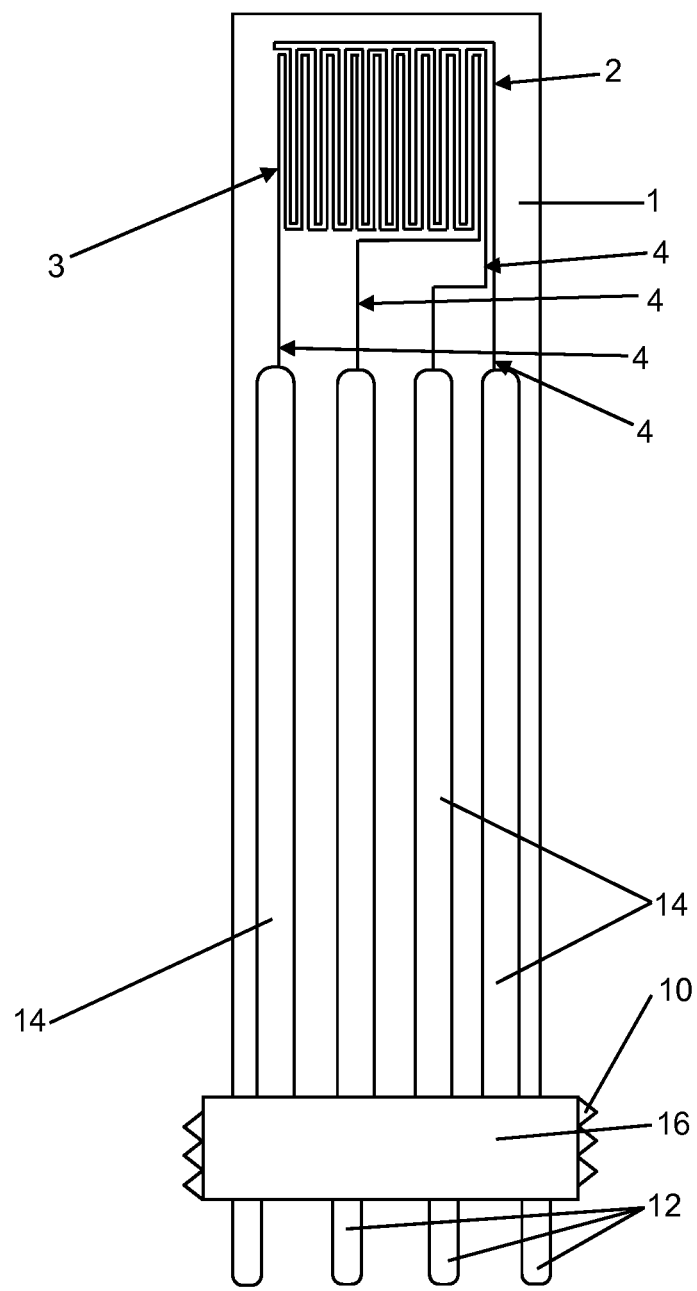
FIG. 5 shows a schematic top view of a soot sensor, according to an embodiment of the present invention.

FIG. 5 shows a schematic top view of a soot sensor according to an embodiment of the present invention. The soot sensor has a substrate 1 made from a metal oxide or a metal oxide ceramic, on which two interlaced heating spirals 2, 3, as a meandering structure made from a platinum thick layer, are disposed. The structure of the heating spirals 2, 3 was cut out of a previously contiguous platinum thick layer using a laser beam. The heating spirals 2, 3 are connected to widened conductive layers 14 via short leads 4. Due to the relatively narrow lead cross section, the resistance drops primarily at the heating spirals 2, 3 and not at the widened conductive layers 14.

The substrate 1 is fastened in a cylindrical connecting terminal 16 by glass solder or a temperature-stable adhesive (not shown). An external thread 10 for fastening the soot sensor in an exhaust gas system is disposed on the cylindrical jacket of the connecting terminal 16. The widened conductive layers 14 are connected in an electrically conductive manner to plugs 12, via which the heating spirals 2, 3 may be acted upon with an electrical voltage.

By using a laser beam to structure the heating spirals 2, 3, the two heating spirals 2, 3 may be created so as to have a spacing distance between 10 μm and 30 μm. Due to the narrow spacing distance, the sensitivity of the soot sensor is increased as compared to conventionally produced soot sensors having spacing distances of approximately 80 μm to 100 μm between the heating spirals.

Figure 6:
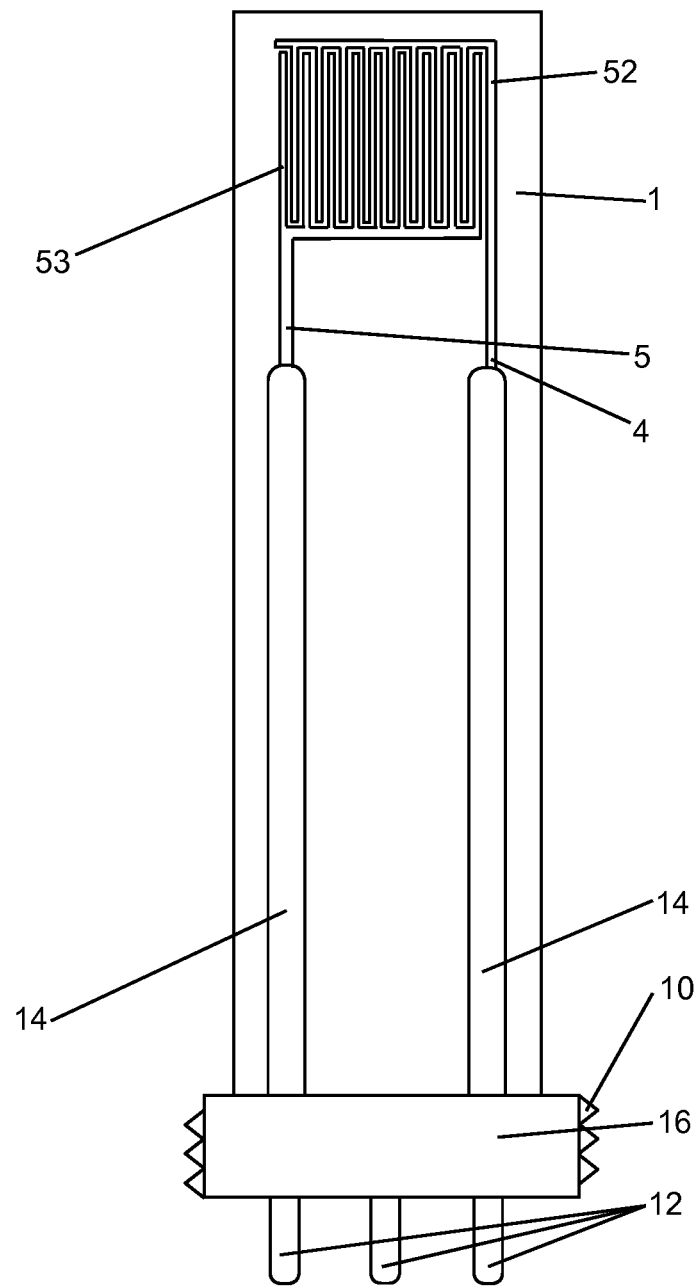
FIG. 6 shows a schematic top view of a soot sensor including a temperature sensor, according to an embodiment of the present invention.

FIG. 6 shows a schematic top view of another soot sensor according to an embodiment of the present invention. Metallic structures made from platinum or a platinum alloy are applied on an electrically insulating substrate 1 made from a metal oxide, preferably aluminum oxide. Two electrodes 52, 53, as the metallic structures, are disposed on the insulating substrate 1, the electrodes having an interlaced comb structure and each of which is contiguous in and of itself. The electrodes 52, 53 are electrically contacted to leads 4, 5. The electrodes 52, 53 and the leads 4, 5 already form a soot sensor on the electrically insulating substrate 1.

A meandering structure (not shown in FIG. 6) is formed on the back side of the ceramic substrate 1 and forms a temperature sensor. The temperature sensor is preferably a platinum resistor structure.

The combination sensor formed by the comb electrodes 52, 53 and the temperature sensor 7 may be fastened via a thread 10 in an opening of an exhaust gas pipe (not shown) having a suitable mating thread or via a holder having a corresponding mating thread. The temperature sensor and the electrodes 52, 53, in the installed state thereof, point into the interior of the exhaust gas pipe. On the exterior, the soot sensor has three plugs 12, which are electrically connected to the leads 4, 5 for the electrodes and to the leads for the temperature sensor. By a through-plating through the ceramic substrate 1, the plug 12 connected to the leads 5 is also used for the electrical contacting of one end of the temperature sensor.

All leads 4, 5 lead into widened conductive layers 14, which are disposed between the leads 4, 5, 6 and the plugs 12. By such widening, it is ensured that the electrical resistance is caused primarily by the temperature sensor and the electrodes 52, 53 and, therefore, the electrical voltage drops substantially at the temperature sensor and the electrodes 52, 53. The length of the insulating substrate 1 and the widened conductive layers 14 (from the top to the bottom in FIG. 6) is intended to thermally insulate the soot sensor toward the connecting terminal 16, which contains the plug 12 and the thread 10. It is also sufficient to select the length of the soot sensor such that the insulation and the plugs 12 are not damaged by the heat of the exhaust gas.

The plugs 12 extend through the connecting terminal 16 and are electrically connected to the widened conductive layers 14, for example, in that the wires are soldered or welded on. The connecting terminal 16 may be, for example, a ceramic plug having through-holes for wires, or having enclosed wires for the electrical contacting of the plugs 12 to the widened conductive layers 14. The connecting terminal 16 is connected to the insulating ceramic substrate 1 in a mechanically fixed and rigid manner by a glazing made from an $SiO_2$ glass (not shown). The glazing is used to connect the connecting terminal 16 to the insulating substrate 1, but also fixes and protects the connecting wires between the plugs 12 and the widened conductive layers 14 and seals the connecting terminal 16 with respect to the outside (in the direction of the plug 12).

The spacing distances between the electrodes 52, 53 are shown in an enlarged view in the schematic illustration according to FIG. 6 and are actually only approximately 30 μm to 50 μm in size. The electrodes 52, 53 are separated from one another by a laser beam, wherein the width of the focal point thereof determines the spacing distance between the electrodes 52, 53. The conductive tracks of the electrodes 52, 53 and the leads 4, 5 are depicted in FIG. 6 as surfaces, in contrast to FIG. 1. The width of the surfaces does not correspond to the actual width of the conductive tracks and, in particular, the spacing distances of the electrodes 52, 53 according to the present invention are substantially finer than depicted in the overview of the schematic FIG. 6.

When a measurement is carried out, the electrical DC resistance between the comb electrodes 52, 53 and/or the capacitance between the two comb electrodes 52, 53 is measured. The capacitance may be measured, for example, by an LC oscillating circuit. If soot particles settle on the surface of the insulating substrate 1 between the electrodes 52, 53, the electrical resistance between the electrodes 52, 53 or the permittivity between the two electrodes 52, 53 changes, which becomes apparent in a capacitive measurement.

In a separate heating device (not shown), which may be disposed on the ceramic substrate 1, the ceramic substrate 1 may be heated between measurements to 600° C. to 700° C. As a result, the soot particles on the surface of the ceramic substrate 1 burn off between the electrodes 52, 53. That is, the surface of the ceramic substrate 1 is burned free between the electrodes 52, 53. The electrical resistance and/or the capacitance between the electrodes 52, 53 and the change over time thereof may then be determined again in order to determine the soot-particle concentration and its change over time in the exhaust gas flow.

In the pauses therebetween or, if the influences of the operation of the electrodes 52, 53 are suitably computationally accounted for, simultaneously therewith, the temperature of the exhaust gas flow may be determined by the temperature sensor 7.

The electrodes 52, 53 and the temperature sensor 7 are produced, for example, by first applying a platinum layer or a platinum alloy layer, as a thick layer, on the ceramic substrate 1. Next, the structure shown in FIG. 6 is created by a laser or a laser beam by vaporizing the free areas between the electrodes 52, 53, which are shown in FIG. 6, by the laser beam. To do this, the laser beam is focused onto the surface of the platinum layer or the platinum alloy layer. The structures that are shown may also be prestructured by a suitable printing method, with which the thick layer is applied, such that only the small spacing distances between the comb electrodes 52, 53 of the soot sensor need to be burned free with the laser.

The user of a laser makes it possible to create very narrow spacings between the electrodes 52, 53 of the soot sensor, which increases the sensitivity of the soot sensor.

Figure 7:
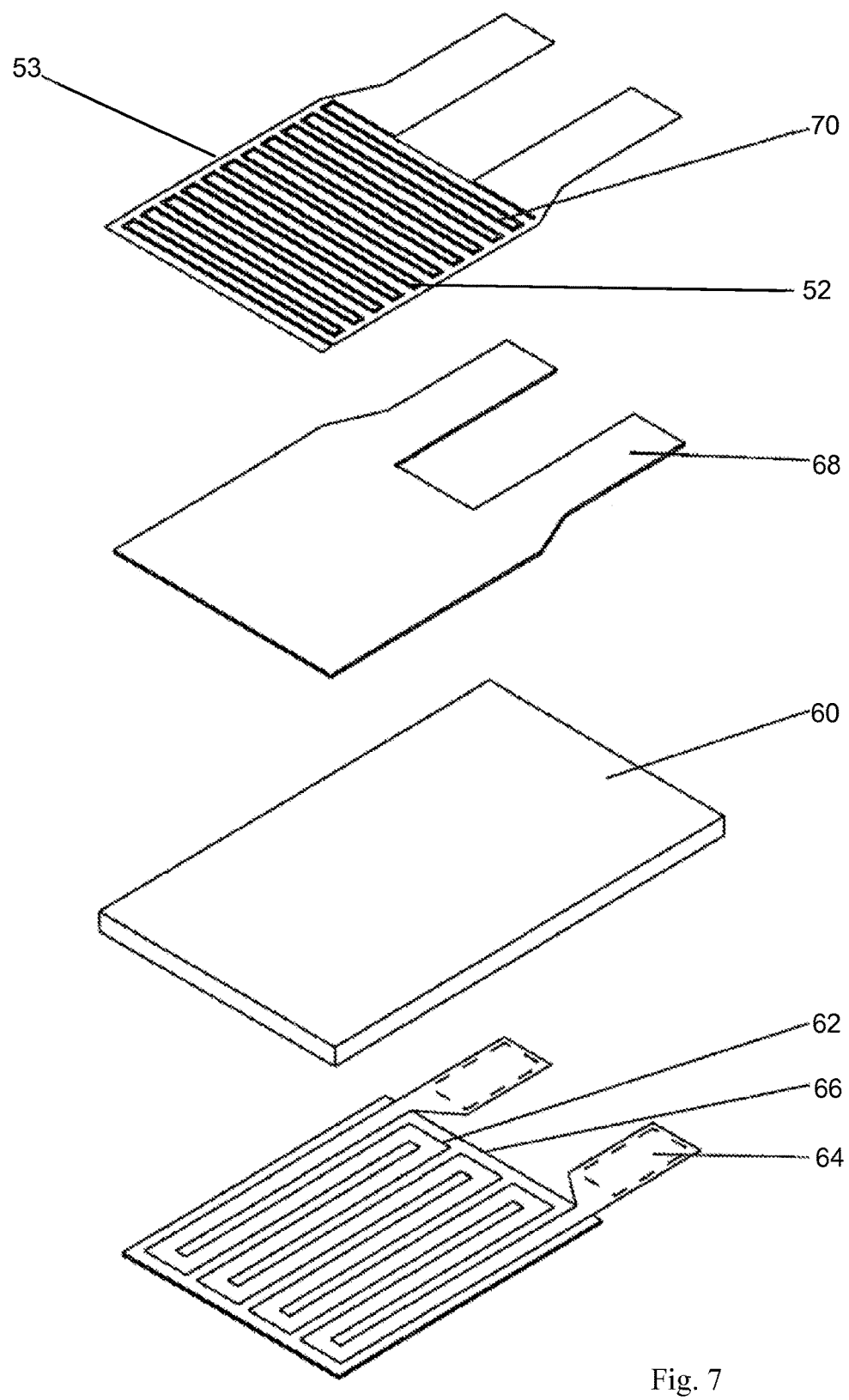
FIG. 7 shows a schematic perspective exploded view for the purpose of explaining a method according to an embodiment of the present invention.

FIG. 7 shows a schematic perspective, exploded view for the purpose of explaining a method according to an embodiment of the present invention. A heater 62 having two contact pads 64 is applied onto the underside (on the bottom in FIG. 7) of a substrate 60 made from $Al_2O_3$. The heater 62 may be printed on, for example, using a thick-layer technology, as a metallic layer.

The heating spirals of the heater 62 are covered with a passivation 66, such that the heater 62 is protected on both sides by the $Al_2O_3$ substrate 60 and the passivation 66 in the manner of a sandwich structure. A ceramic plate, for example, may be bonded on as the passivation 66.

A prestructured platinum thick layer 68 is applied onto the top side (at the top in FIG. 7) of the substrate 60. In a subsequent step, this platinum thick layer 68 is separated into two parts, which are electrically insulated from one another, by a laser beam, which is guided along an unbroken line over the platinum thick layer 68. The result thereof is a laser-structured platinum thick layer 70, which has two mutually engaged comb electrodes 52, 53. The use of the laser makes it possible to obtain extremely narrow spacing distances between the electrodes 52, 53 of less than 50 μm. At the same time, given a consistent surface of the substrate 60, it is therefore possible to produce comb electrodes 52, 53 having a greater number of comb teeth such that the structure 70 that is produced has a larger electrode surface. Due to the narrower spacing distances of the electrodes 52, 53 and the larger electrode surface, the electrical insulation between the electrodes 52, 53 decreases and, therefore, the sensitivity of the soot sensor increases.

If soot particles settle via adsorption on the surface of the thusly produced soot sensor, the soot particles will also settle in the intermediate spaces between the electrodes 52, 53, which were burned free or vaporized with the laser. The longer this line—which was created by the laser—between the electrodes 52, 53 is, the greater the statistical probability is that settling will occur between the electrodes 52, 53.

If soot particles settle in these intermediate spaces between the electrodes 52, 53, this induces a change in resistance and, if there is a sufficient number of soot particles or if a sufficient surface area of the intermediate spaces is covered with soot particles, this induces a measurable signal in the form of an electrical insulation loss. The soot sensor has greater sensitivity due to the narrow spacing distances and the longer length of the intermediate spaces of the spacings between the electrodes 52, 53.

FIG. 7 shows, indirectly, an exploded view of a sensor according to an embodiment of the present invention. If one imagines that the unstructured platinum layer 68 is not there, an exploded view of a soot sensor according to an embodiment of the present invention is shown in FIG. 7.

The features of the invention disclosed in the aforementioned description, and in the claims, figures, and exemplary embodiments may be essential, individually or in any combination thereof, to the realization of the invention in the various embodiments thereof.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:
1. A method for producing a soot sensor comprising contact elements (12) and a temperature sensor (7), the method comprising:
   applying a contiguous metallic layer on an electrically insulating substrate (1, 20); and
   structuring the metallic layer with a laser beam by vaporizing areas of the metallic layer,
      wherein at least two interlaced contiguous electrically conductive heating spirals (2, 3, 42) are produced for determining an amount of soot between the heating spirals,
      wherein the heating spirals (2, 3, 42) are spatially separated from one another by the laser beam and are electrically insulated from one another, such that at least portions of the heating spirals (2, 3, 42) substantially extend next to one another and within a distance of less than 50 µm to one another, and
      wherein the heating spirals (2, 3, 42) are electrically contacted to a measuring element such that the electrical insulation losses between the heating spirals (2, 3, 42) are measurable for determining the concentration of soot particles in a gas flow,
      wherein the temperature sensor (7) is disposed on the electrically insulating substrate (1) adjacent to the heating spirals (2, 3, 42), and
      wherein a portion of a common lead (5, 8) electrically contacting one of the heating spirals (3) and the temperature sensor (7) to one of the contact elements (12) is used jointly for the one of the heating spirals (3) and for the temperature sensor (7).

2. The method according to claim 1,
   wherein the metallic layer is applied in a prestructured manner onto the electrically insulating substrate (1, 20), and
   wherein at least widened conductive layers (14) are prestructured for electrical contacting of the heating spirals (2, 3, 42).

3. The method according to claim 1,
   wherein the laser beam is moved over the metallic layer in a line along a spacing between the heating spirals (2, 3, 42) to be produced,
   wherein the metallic layer is thereby vaporized along the line, and
   wherein a distance of the spacing between the produced heating spirals (2, 3, 42) corresponds to a diameter of an effective cross section of a focal spot of the laser beam.

4. The method according to claim 3, wherein the line is a meandering line.

5. The method according to claim 1, wherein the heating spirals (2, 3, 42) extend next to one another along at least 90% of the total length thereof.

6. The method according to claim 1, wherein a metal oxide substrate (1, 20) or a glass substrate (20) is used as the electrically insulating substrate (1, 20).

7. The method according to claim 6, wherein the metal oxide substrate (1, 20) is a ceramic $Al_2O_3$ substrate or $Al_2O_3$ layer or wherein the glass substrate (20) is a material selected from the group consisting of a glass and glass ceramic.

8. The method according to claim 1, wherein after the structuring of the heating spirals (2, 3, 42), leads (4, 5, 14) of the heating spirals (2, 3, 42) are coated entirely.

9. The method according to claim 8, wherein the heating spirals (2, 3, 42) are coated in certain areas with an insulating layer (21) of a material selected from the group consisting of a metal oxide, a glass, and a glass ceramic and, wherein a temperature sensor (7) is fastened on the insulating layer (21).

10. The method according to claim 1,
    wherein a layer structure formed by the contiguous metallic layer and the electrically insulating substrate (1, 20) is fastened on a connecting terminal (16), and
    wherein the heating spirals (2, 3, 42) are electrically contacted to contact elements (12) of the connecting terminal (16).

11. A soot sensor produced by applying a contiguous metallic layer on an electrically insulating substrate (1, 20) and structuring the metallic layer with a laser beam by vaporizing areas of the metallic layer, the soot sensor comprising:
    a connecting terminal (16);
    a temperature sensor (7);
    the electrically insulating substrate (1, 20); and
    at least two contiguous electrically heating spirals (2, 3, 42) spatially separated from one another by the laser beam and interlaced as structured metallic layers for determining an amount of soot between the heating spirals,
       wherein the heating spirals (2, 3, 42) are electrically insulated from one another, wherein at least portions of the heating spirals (2, 3, 42) substantially extend next to one another and within a distance of less than 50 μm to one another, wherein an intermediate space between the heating spirals (2, 3, 42) is burned free with the laser beam, the heating spirals (2, 3, 42) being contacted to widened conductive layers (14);

wherein the heating spirals (2, 3, 42) are electrically contacted to a measuring element such that the electrical insulation losses between the heating spirals (2, 3, 42) are measurable for determining the concentration of soot particles in a gas flow, wherein the heating spirals (2, 3, 42) are disposed as the structured metallic layers on the electrically insulating substrate (1, 20) and are covered at least in areas with an insulating layer (21), wherein the temperature sensor (7) is disposed as a structured metallic layer on the insulating layer (21) or wherein the heating spirals (2, 3, 42) and the temperature sensor (7) are disposed on the same electrically insulating substrate (1, 20), wherein the temperature sensor (7) and the heating spirals (2, 3, 42) are electrically and mechanically connected to the connecting terminal (16), and wherein a portion of a common lead (5, 8) electrically contacting one of the heating spirals (3) and the temperature sensor (7) to the connecting terminal (16) is used jointly for the one of the heating spirals (3) and for the temperature sensor (7).

12. The soot sensor according to claim 11, wherein at least the widened conductive layers (14) are covered with the insulating layer (21).

13. The soot sensor according to claim 11, wherein the electrically insulating substrate (1, 20) is a ceramic metal oxide substrate (60).

14. The soot sensor according to claim 11, wherein the heating spirals (2, 3, 42) are precious metal thick layers structured with a laser, and wherein the heating spirals (2, 3, 42) have an electrical resistance of at least 1 Ohm and at most 10 Ohm.

15. An engine comprising a soot sensor according to claim 11, wherein the soot sensor is fastened via a connecting terminal at an opening in an exhaust gas line, such that the soot sensor is disposed in an exhaust gas flow of the engine.

* * * * *